(12) United States Patent
Aoyagi

(10) Patent No.: US 9,149,243 B2
(45) Date of Patent: Oct. 6, 2015

(54) MEDICAL IMAGE DIAGNOSIS APPARATUS AND IMAGE DATA PROCESSING APPARATUS

(75) Inventor: Kota Aoyagi, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 179 days.

(21) Appl. No.: 13/067,334

(22) Filed: May 25, 2011

(65) Prior Publication Data

US 2012/0029337 A1 Feb. 2, 2012

(30) Foreign Application Priority Data

May 25, 2010 (JP) ................. 2010-119572

(51) Int. Cl.
*A61B 6/00* (2006.01)
*G01R 33/56* (2006.01)

(52) U.S. Cl.
CPC ............ *A61B 6/5211* (2013.01); *G01R 33/5608* (2013.01)

(58) Field of Classification Search
CPC ............................ A61B 6/5211; G01R 33/5608
USPC ......... 382/128, 130–134, 173, 174, 254–308, 382/318–321; 600/407–472
See application file for complete search history.

(56) References Cited

U.S. PATENT DOCUMENTS

2008/0253630 A1* 10/2008 Masumoto et al. ........... 382/128
2010/0041989 A1* 2/2010 Sehgal et al. ................. 600/439

FOREIGN PATENT DOCUMENTS

JP 2010-075549 4/2010

* cited by examiner

*Primary Examiner* — Mark Remaly
(74) *Attorney, Agent, or Firm* — Oblon, McClelland, Maier & Neustadt, L.L.P.

(57) ABSTRACT

A medical image diagnosis apparatus and an image data processing apparatus that diagnoses vascular invasion status of a tumor and decides the most appropriate therapy method for the tumor by extracting tumor candidate regions and vascular regions based on extensive volume data derived from covering a therapy target organ, and specifying an adjacent vascular region existing within a prescribed scope from a gravity center of a tumor. The tumor candidate regions and vascular regions are generated as 3D image data or MPR image data for submitting a recommended therapy method for the tumor by adding branch data of the adjacent vascular.

13 Claims, 11 Drawing Sheets

MEDICAL IMAGE DIAGNOSIS APPARATUS AND IMAGE DATA PROCESSING APPARATUS

CROSS-REFERENCE TO RELATED APPLICATIONS

This application claims the benefit of priority under 35 U.S.C. §119(a) from Japanese Patent Application No. 2010-119572 filed May 25, 2010, the contents of which are expressly incorporated herein by reference in their entirety.

BACKGROUND OF THE INVENTION

A. Field of the Invention

Embodiments consistent with the present invention relate to a medical image diagnosis apparatus and an image data processing apparatus that can generate and display efficacious therapy assist data for a tumor (cancer) therapy.

B. Background of the Invention

Recently, with developments of a living body data detection unit and an operation process units operating at high speeds and with high level functions, medical image diagnosis using such as an X-ray computer tomography (CT) apparatus or a magnetic resonance imaging (MRI) apparatus can acquire 3 dimensional data (volume data) in a short time. Consequently, such a medical diagnosis can perform early recognition of malignant tumors, such as a liver cancer. Generally, therapy methods for malignant tumors by using such medical image diagnosis are decided based on tumor numbers, tumor sizes and existence or non-existence of vessel invasions into blood vessels and lymph vessels adjacent to the tumor (hereinafter, referred to as "adjacent vascular") and a progress level of the vascular invasion.

Thus, the differential diagnosis for a tumor is performed based on the tumor numbers, tumor sizes and vessel invasions. For instance, since the vessel invasion is a prognostic factor for a liver cancer, the pre-treatment diagnosis for a vessel invasion, in particular, a portal invasion is extremely important for deciding the therapy policy.

Further, an accuracy of the recent differential diagnosis for a tumor has largely improved by observing image data acquired through a patient who is dosed with an contrast enhance agent. For instance, a contrast enhance agent for the ultrasound wave imaging, such as Sonazoid and a contrast enhance agent for the MR imaging, such as GD-EOB-DTPA have been developed for displaying a liver cancer with enhanced contrast. Further, it has been proposed to differentiate an extent of the tumor and a grade of the tumor malignancy by extracting 3D image data of the tumor that is enhanced by the contrast enhance agent. For instance, a differential diagnosis supporting method for a tumor has been proposed by performing automatic analysis of brightness variation of image patterns that appear in the tumor regions due to the inflow of the contrast enhance agent (for example, Japanese Patent Application Publication 2010-5263).

However, the proposed differential diagnosis for a tumor by using the contrast enhance agent has mainly observed the extent of the tumor and the grade of malignancy based on blood flowing status in the tumor itself. Thus, the proposed differential diagnosis for a tumor cannot obtain the prognostic factor of vascular invasion data adjacent the tumor. Consequently, it has been very difficult to decide the most appropriate therapy for the tumor.

SUMMARY OF THE INVENTION

To solve the above-noted problems and drawbacks, the embodiments consistent with the present invention provide a medical image diagnosis apparatus, an image data processing apparatus that can generate and display efficacious therapy assist data for a tumor therapy and a method for controlling display of the therapy assist data of a patient, based on volume data acquired from therapy target organs.

Accordingly, there is provided one embodiment of a medical image diagnosis apparatus including;

a volume data generation unit configured to generate volume data in time series based on image data acquired from a therapy target organ;

a vascular region detection unit configured to detect vascular regions in the therapy target organ based on extensive volume data of vascular enhanced phases selected among the volume data generated in time series;

a tumor candidate region detection unit configured to detect tumor candidate regions in the therapy target organ based on extensive volume data of tumor enhanced phases selected among the volume data generated in time series;

a tumor position data measuring unit configured to detect each gravity center of the tumor candidate regions;

an adjacent vascular detection unit configured to detect the vascular regions existing within a prescribed range from each gravity center of the tumors as adjacent vascular regions; and an image data generation unit configured to generate therapy assisting image data based on volume data including the tumor candidate regions and the adjacent vascular regions extracted from the extensive volume data.

In another embodiment, there is provided medical image diagnosis apparatus including;

a volume data generation unit configured to generate volume data in time series based on image data acquired from a therapy target organ;

a vascular region detection unit configured to detect vascular regions in the therapy target organ based on volume data of a vascular enhanced phase selected among the volume data generated in time series;

a tumor candidate region detection unit configured to detect tumor candidate regions in the therapy target organ based on volume data a of tumor enhanced phase selected among the volume data generated in time series;

a tumor position data measuring unit configured to detect gravity centers of the tumor candidate regions;

an adjacent vascular detection unit configured to detect vascular regions existing within a prescribed range from each of gravity center of the tumors as an adjacent vascular region;

a tumor parameter calculation unit configured to calculate at least one tumor parameter based on at least one of the tumor candidate region data, the vascular region data and the adjacent vascular region data; and a therapy method set-up unit configured to set up at least one therapy method for the tumor candidate regions based on the tumor parameter.

Further, there is provided an embodiment of image data processing apparatus including;

a volume data storage unit configured to store volume data acquired from a therapy target organ in time series;

a vascular region detection unit configured to detect vascular regions in the therapy target organ based on extensive volume data of vascular enhanced phases selected among the volume data generated in time series;

a tumor candidate region detection unit configured to detect tumor candidate regions in the therapy target organ based on the extensive volume data of tumor enhanced phases selected among the volume data generated in time series;

a tumor position data measuring unit configured to detect a gravity center of each tumor candidate region;

an adjacent vascular detection unit configured to detect a vascular region located within a prescribed range from the tumor gravity center as an adjacent vascular region; and an image data generation unit configured to generate therapy assist data based on volume data including the tumor candidate regions and the adjacent vascular region that are extracted from the extensive volume data.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings.

DESCRIPTION OF PREFERRED EMBODIMENTS

A medical image diagnosis apparatus according to one embodiment of the present invention detects tumor candidate regions by selecting tumor enhanced phases among extensive volume data acquired in time series through an MR imaging for covering a whole therapy target organ in a patient (hereinafter simply referred to as "extensive volume data"). The image diagnosis apparatus, further detects adjacent vascular regions to the tumor candidate regions by selecting vascular enhanced phases based on the extensive volume data. Further, the image diagnosis apparatus calculates various tumor parameters based on sizes of the detected tumor candidate regions and position data of the detected adjacent vascular regions for setting up recommended therapy policies for the tumors. The recommended therapy policy data and narrow scope volume data for covering the tumor candidate regions and the adjacent vascular regions (hereinafter simply referred to as "narrow scope volume data") are displayed on a display as therapy assist data. The therapy assist data is displayed as 3D (dimensional) image data or multi planar reconstruction (MPR) image data.

In the following embodiments, generation and display of the therapy assist data are exemplarily performed based on volume data acquired through a magnetic resonance (MR) imaging to a therapy target organ. Of course, it is possible to acquire the volume data through another imaging modality, such as an X-ray CT imaging.

Figure 1:
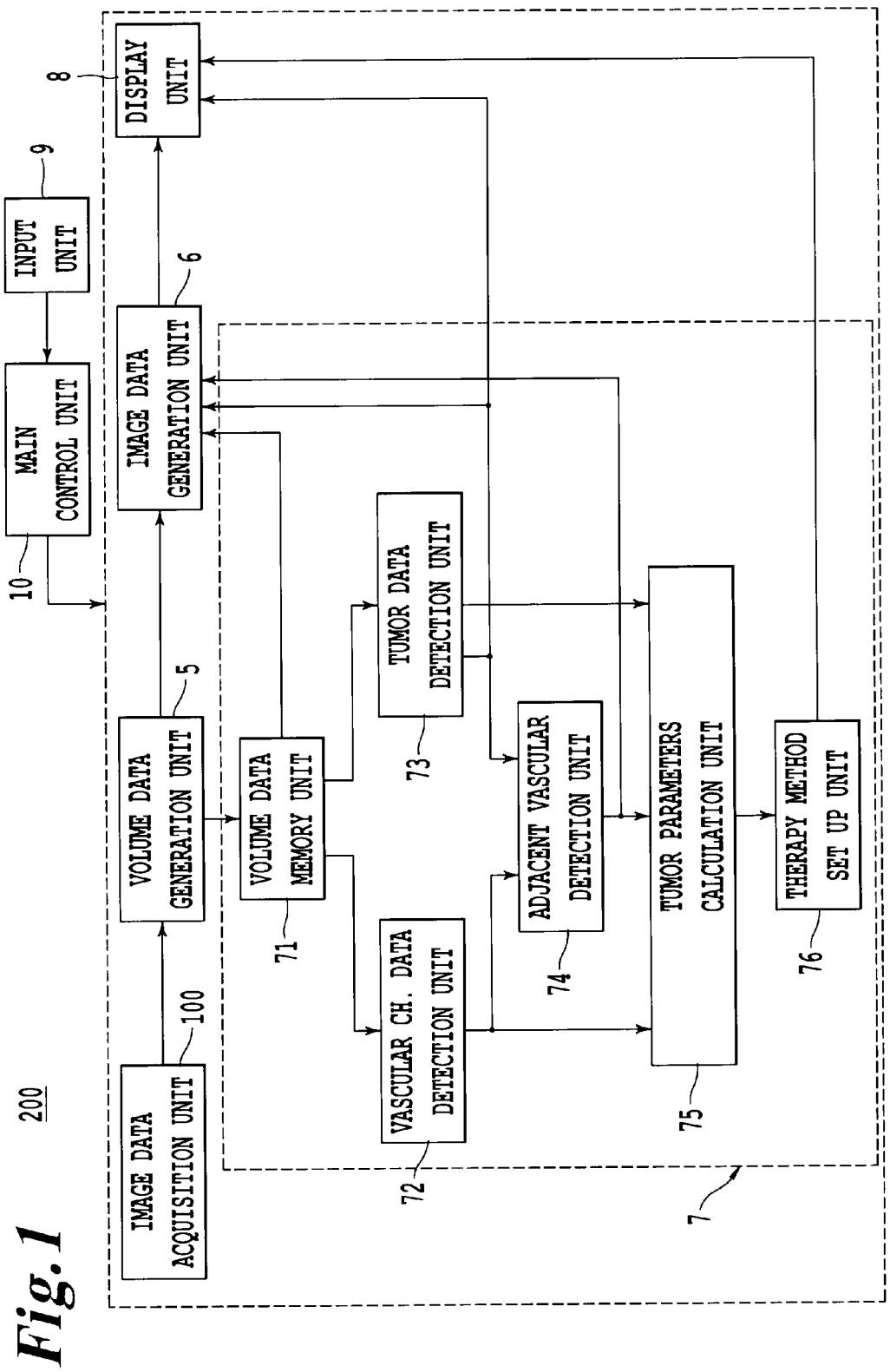
FIG. 1 is a block diagram illustrating a medical image diagnosis apparatus according to an embodiment of the present invention.

FIG. 1 illustrates a block diagram illustrating a system construction of a medical image diagnosis apparatus 200 consistent with one embodiment of the present invention. The image diagnosis apparatus 200 includes an image data acquisition unit 100, a volume data generation unit 5, an image data generation unit 6, a data processing unit 7, a display unit 8, an input unit 9 and a main control unit 10. The image data acquisition unit 100 acquires MR data as image data by performing 3 dimensional MR imaging over a therapy target organ of a patient who is administered with a contrast enhance agent. The volume data generation unit 5 generates volume data based on MR data acquired in a time series. The image data generation unit 6 generates extensive volume data for covering the whole therapy target organ by processing volume data generated in the volume data generation unit 5. Further, as explained later, the image data generation unit 6 generates narrow scope 3D image data and multi planar reconstruction (MPR) image data that are centered on the tumor candidate region in the therapy target organ. The data processing unit 7 detects tumor candidate regions and vascular regions in the therapy target organ by selecting tumor enhanced phases and vascular enhanced phases among the volume data acquired in time-series. These enhanced phases are selected in accordance with changes of image brightness due to the inflow of the contrast enhance agent. Further, the data processing unit 7 sets up recommended therapy policies suitable for the tumors. A more detailed functional description of the data processing unit 7 explain the later. The display unit 8 displays 3D image data and MPR image data generated in the image data generation unit 6 and the recommended therapy policies set up by the data process unit 7 as therapy assist data for the tumor. The input unit 9 sets up acquisition conditions of the volume data and generation conditions for the image data. The main control unit 10 totally controls the above-mentioned units.

Figure 2:
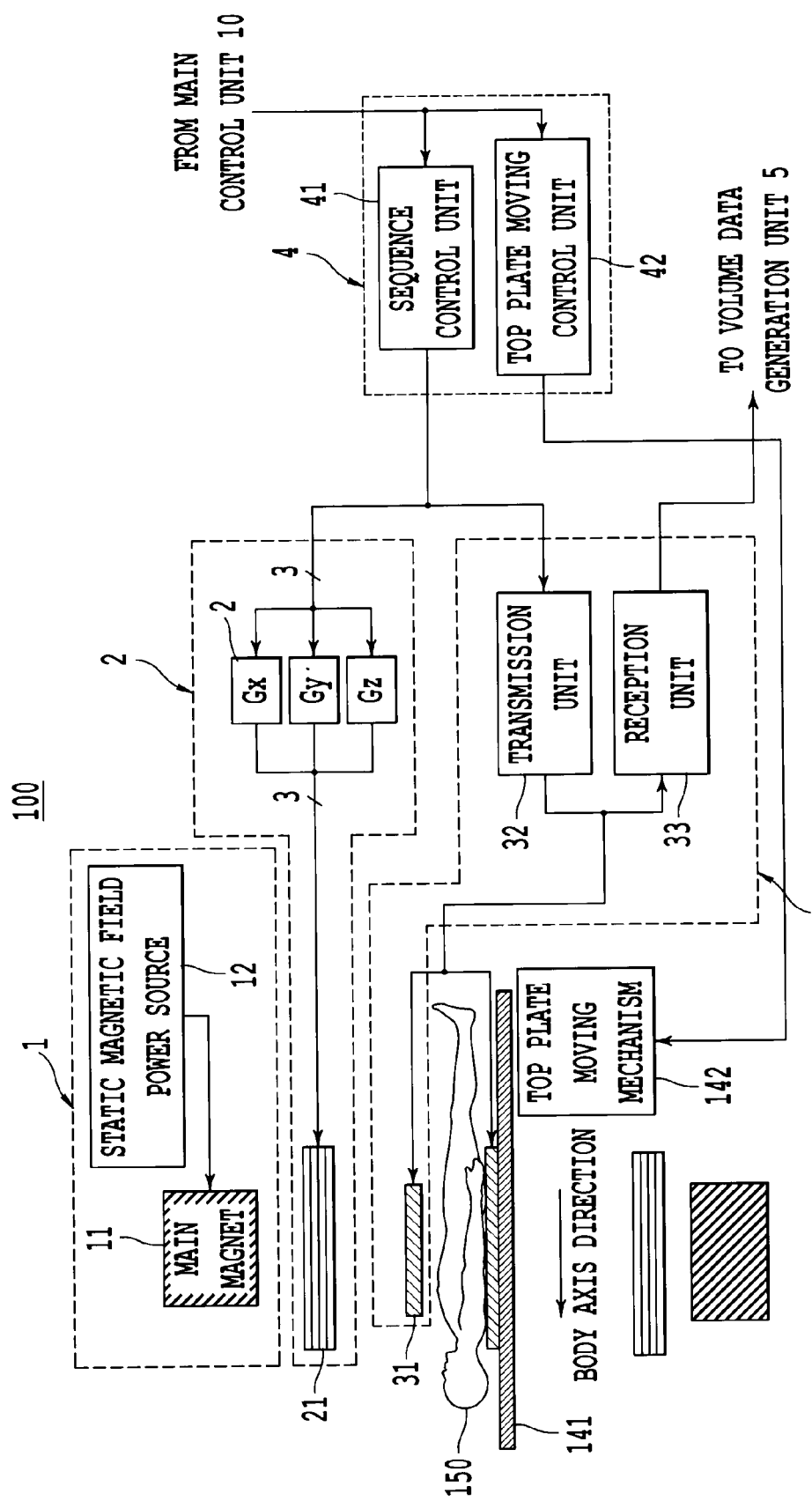
FIG. 2 is a block diagram illustrating a construction of an image data acquisition unit provided in the medical image diagnosis apparatus shown in FIG. 1.

FIG. 2 is a block diagram illustrating a construction of the image data acquisition unit 100 for acquiring MR image data by performing MR imaging to a therapy target organ of a patient. The image data acquisition unit 100 includes a static magnetic field generation unit 1, a gradient magnetic field generation unit 2, a transmission/reception unit 3, a top plate 141, a top plate moving mechanism 142 and a sub-control unit 4. The static magnetic field generation unit 1 generates a static magnetic field on a therapy target organ of a patient 150. The gradient magnetic field generation unit 2 generates gradient magnetic fields on a therapy target organ of a patient 150. The transmission/reception unit 3 irradiates RF (radio frequency) pulses on the therapy target organ and detects generated MR signals. The top plate 141 supports the patient

150. The top plate moving mechanism 142 moves the top plate 141 along a body axis direction of the patient 150 (the z-axis direction in FIG. 2). The sub-control unit 4 controls pulse sequences of MR imaging and movements of the top plate 141.

The static magnetic field generation unit 1 includes a main magnet 11 constructed by a resistive magnet or a superconductive magnet and a static magnetic field power source 12 for supplying currents to the main magnet 11 for providing a strong static magnetic field on a therapy target organ of a patient 150 placed in an imaging field of a gantry center portion (not shown). The gradient magnetic field generation unit 2 includes gradient magnetic field coils 21 for forming each gradient magnetic field along a body axis direction (z-axis direction) of the patient 150, an x-axis direction orthogonal to the body axis direction and a y-axis direction orthogonal to the x-axis and z-axis directions and a gradient magnetic field power sources for respectively supplying pulse currents to each of the gradient magnetic field coils 21.

The gradient magnetic field coils 21 and the gradient magnetic field power sources 22 add position data to the imaging field of a gantry center portion in which a therapy target organ of a patient 150 is placed. Thus, the gradient magnetic field power source 22 generates gradient magnetic fields to each direction by controlling pulse currents supplied to each of gradient magnetic field coils 21 in each of the x-axis direction, the y-axis direction and the z-axis direction based on the sequence control signals supplied from the sub-control unit 4. The gradient magnetic fields in each of the x-axis direction, the y-axis direction and the z-axis direction are composed so as to generate a slice selection gradient magnetic field, a phase encoded gradient magnetic field and a frequency encoded (read out) gradient magnetic field that orthogonally cross each other. These gradient magnetic fields are overlapped with the static magnetic field generated by the main magnet 11 and supplied on a therapy target organ of a patient 150.

The transmission/reception unit 3 includes a transmission/reception coil 31, a transmission unit 32 and a reception unit 33. The transmission/reception coil 31 irradiates RF pulses on the therapy target organ of the patient 150 and detects MR signals generated from the therapy target organ. The transmission unit 32 and the reception unit 33 are connected to the transmission/reception coil 31. The transmission unit 32 includes a reference signal generator, a modulator and a power amplifier (all not shown) for supplying pulse currents to the transmission/reception coil 31. The reference signal generator generates reference signals having the same frequency with the magnetic resonance frequency (Larmor frequency) decided by the static magnetic field strength of the main magnet 11. The modulator generates pulse currents by modulating the reference signals with a prescribed selective excitation waveform. The generated pulse currents are supplied to the transmission/reception coil 31 through the power amplifier so that RF pulses are irradiated on the therapy target organ of the patient 150.

The reception unit 33 generates MR data by performing signal processes of MR signals generated from the therapy target organ by irradiating RF (radio frequency) pulses and detected by the transmission/reception coil 31. Thus, MR signals undergo signal processes by the reception unit 33, such an intermediate frequency conversions, phase detections, low-frequency amplifications, filtering and A/D (analog/digital) conversions. The sub-control unit 4 includes a sequence control unit 41 and a top plate moving control unit 42. The sequence control unit 41 includes a CPU (central processing unit) and a memory circuit (both not shown). The memory circuit stores volume data acquisition conditions supplied from the main control unit 10. Based on the stored data, the sequence control unit 41 generates sequence control signals for MR imaging and controls the gradient magnetic field power source 22 in the gradient magnetic field generation unit 2 and the transmission unit 32 in the transmission/reception unit 3. The top plate moving control unit 42 generates top plate moving control signals based on top plate moving command signals supplied from the input unit 9 through the main control unit 10 and supplies such signals to the top plate moving mechanism 142.

Figure 3:
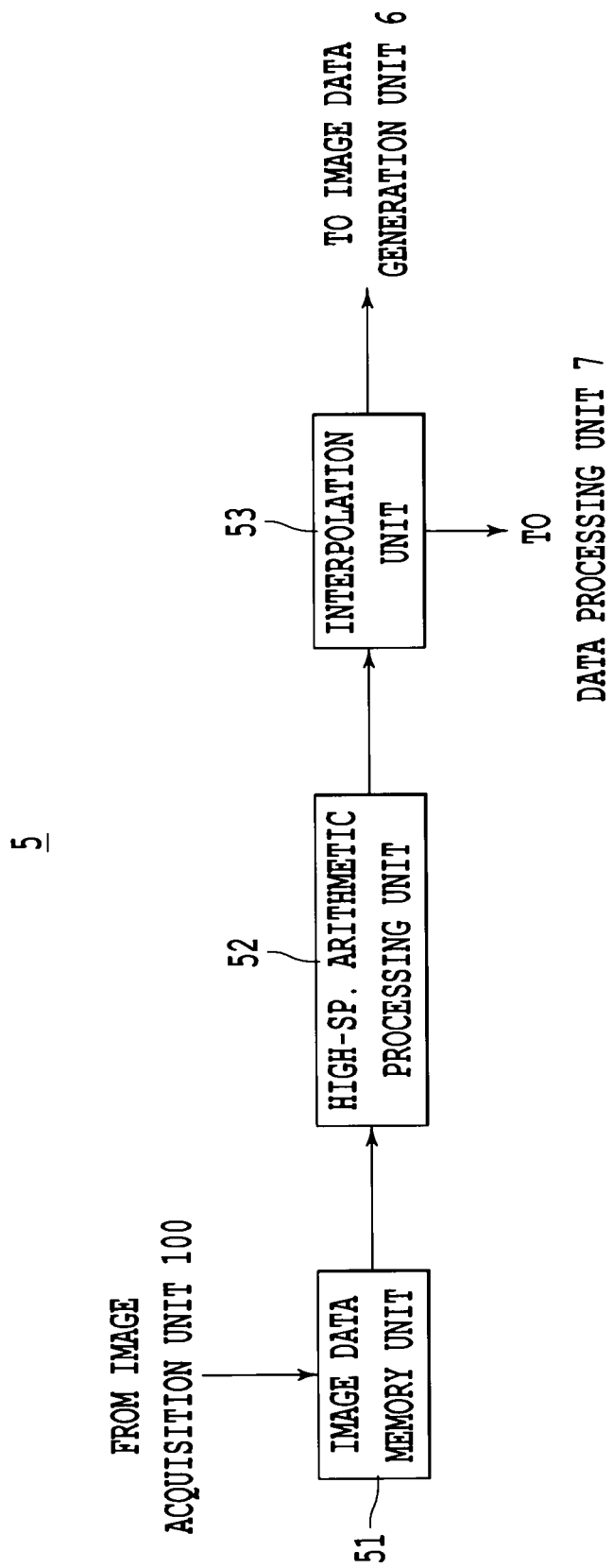
FIG. 3 is a block diagram illustrating a construction of a volume data generation unit provided in the medical image diagnosis apparatus shown in FIG. 1.

FIG. 3 depicts a construction of the volume data generation unit 5 shown in FIG. 1. The volume data generation unit 5 includes an image data memory unit 51, a high speed arithmetic processing unit 52 and an interpolation processing unit 53. The image data memory unit 51 stores MR data sequentially acquired from the therapy target organ by sequentially renewing the slice selection gradient magnetic field and the phase encode gradient magnetic field as 3D image data. The high speed arithmetic processing unit 52 generates 3 dimensional (3D) data of a real space by performing reconstruction processing of a 2D Fourier transform or a 3D Fourier transform to MR data of 3D frequency space (k space) read out from the image data memory unit 51. The interpolation processing unit 53 performs necessary voxel interpolation of the 3D data sequentially generated by the high speed arithmetic processing unit 52 and generates volume data constructed by isotropic voxels. The acquired sequential volume data are supplied to the image data generation unit 6 and the data process unit 7.

Figure 4:
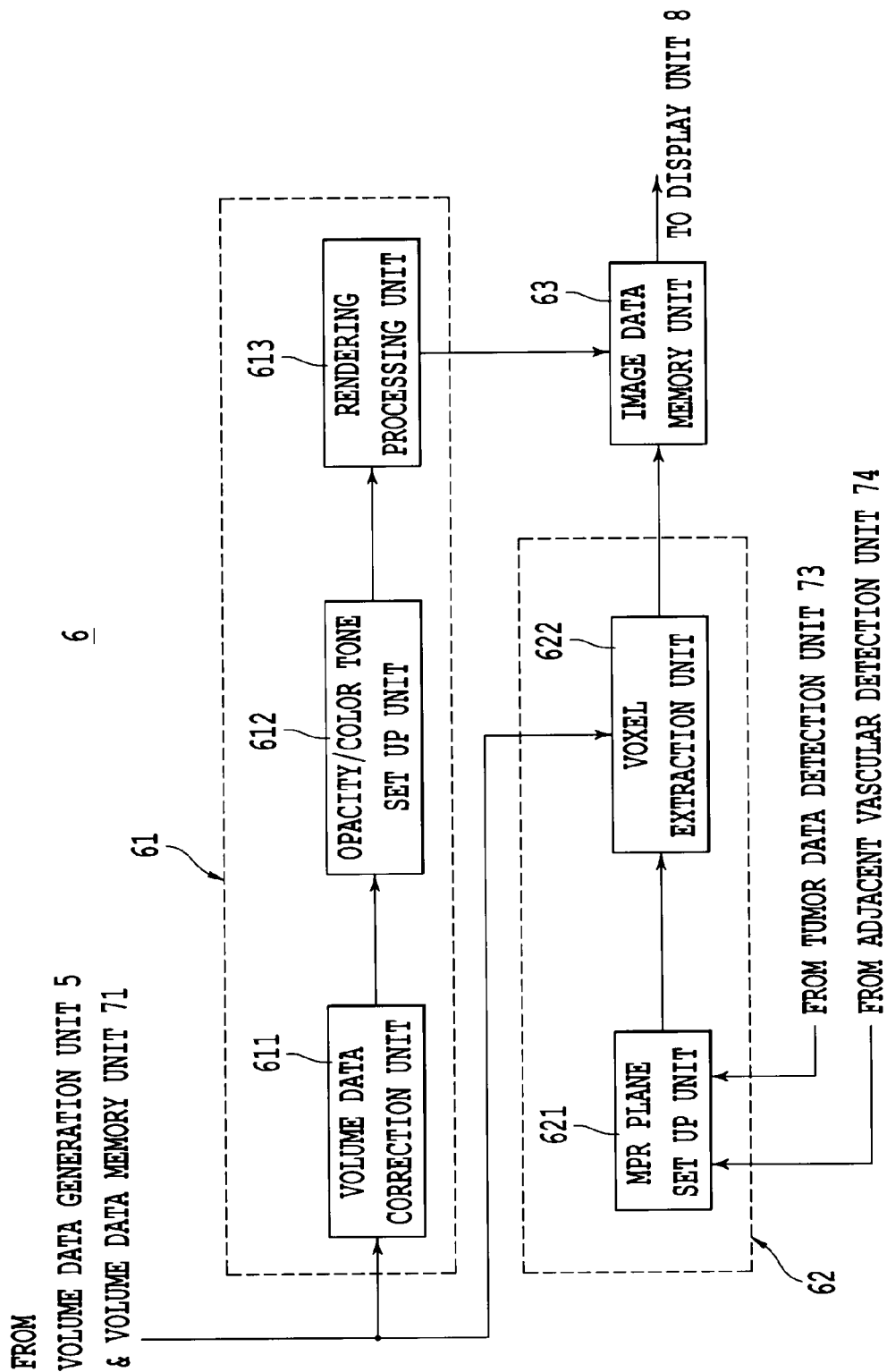
FIG. 4 is a block diagram illustrating an image data generation unit provided in the medical image diagnosis apparatus shown in FIG. 1.

FIG. 4 is a block diagram illustrating a construction of the image data generation unit 6 shown in FIG. 1. The image data generation unit 6 includes a 3D image data generation unit 61, an MPR image data generation unit 62 and an image data memory 63. The 3D image data generation unit 61 generates 3D image data based on volume data supplied from the generation unit 5. The MPR image data generation unit 62 generates MPR image data based on the volume data. The image data memory 63 stores the 3D image data and the MPR image data.

The 3D image data generation unit 61 includes a volume data correction unit 611, an opacity/color tone set-up unit 612 and a rendering process unit 613. The volume data correction unit 611 corrects a voxel value of an extensive volume data covering the therapy target organ that is supplied from the interpolation process unit 53 in the volume data generation unit 5 and a voxel value of a narrow scope volume data that is extracted from the extensive volume data with centering a tumor candidate region of the therapy target organ, based on an inner product value of a prescribed visual line vector for a 3D display and a normal vector to a boundary surface of the organ. The opacity/color tone set-up unit 612 sets up an opacity and a color tone based on the corrected voxel value. The rendering process unit 613 generates an extensive 3D image data and a narrow scope by performing a rendering process of the extensive volume data the of therapy target organ and the narrow scope volume data with centering the tumor candidate regions, based on the opacity and the color tone set up by the opacity/color tone set-up unit 612.

The MPR image data generation unit 62 includes an MPR plane set-up unit 621 and a voxel extraction unit 622. The MPR plane set-up unit 621 receives a gravity center position data of a tumor candidate region supplied from a tumor data detection unit 73 (explained in more detail hereinafter) in the data process unit 7 and a core line data of an adjacent vascular region to the tumor candidate region (hereinafter, referred to as "adjacent vascular") supplied from the vascular detection unit 74 in order to set up a flat MPR plane or a curved MPR plane including a gravity center of the tumor candidate region and a core line of the adjacent vascular region (adjacent core line).

The voxel extraction unit 622 sets up the MPR plane to the extensive volume data of the therapy target organ supplied from the volume data generation unit 5 and extracts voxels of the volume data existing on the MPR plane. Then, the voxel extraction unit 622 generates a narrow scope MPR image data having a gravity center in the tumor candidate region. The extensive 3D image data and the narrow scope 3D image data generated in the 3D image data generation unit 61, and the narrow scope MPR image data generated in the MPR image data generation unit 62 are stored in the image data memory 63. These data are displayed on the display unit 8 as a first therapy assist data for the tumor therapy.

FIGS. 5 to 11 describe exemplary functions of the data processing unit 7. The data processing unit 7 has a detecting function of each size and position of tumor candidate regions in the therapy target organ and each position data of adjacent vascular regions to the tumor candidate regions. Further, the data processing unit 7 has a setting up function of an appropriate therapy policy for the tumor based on these detected data. The detections of the tumor candidate regions and the adjacent vascular regions are performed based on the volume data at timings of brightness changes of the tumor candidate regions (referred to as "tumor enhanced phase") and the volume data at timings of brightness changes of the adjacent vascular regions (referred to as "vascular enhanced phase") that are selected among the volume data generated in time sequences through the volume data generation unit 5.

Figure 5:
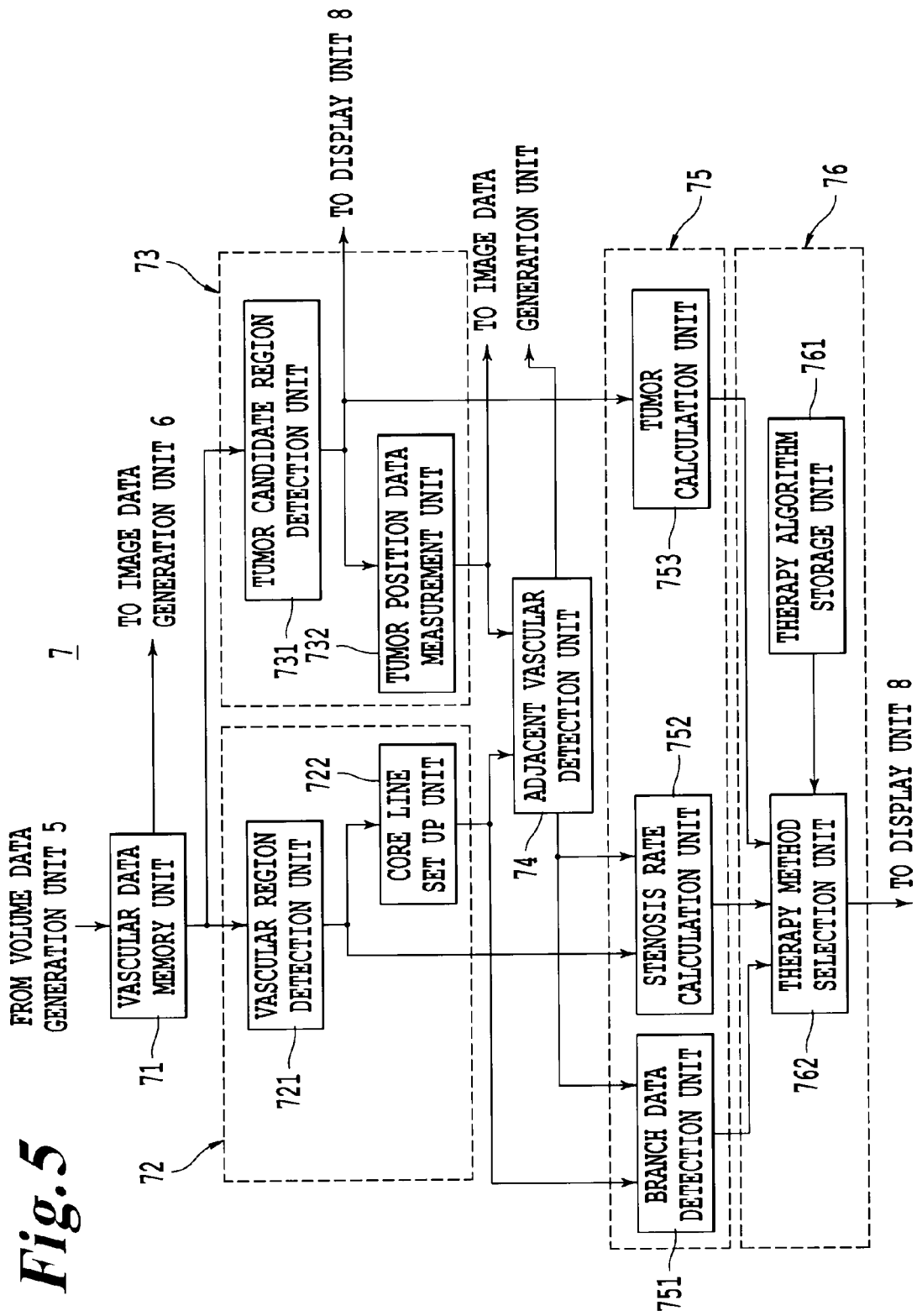
FIG. 5 is a block diagram illustrating a construction of a data process unit provided in the medical image diagnosis apparatus shown in FIG. 1.

FIG. 5 illustrates an exemplary construction of the data processing unit 7. As illustrated in FIG. 5, the data processing unit 7 includes a volume data memory 71, a vascular data detection unit 72, a tumor data detection unit 73, an adjacent vascular detection unit 74, a tumor parameter calculation unit 75 and a therapy method set up unit 76. The volume data memory 71 stores volume data of tumor enhanced phase selected among volume data sequentially generated by the volume data generation unit 5 and volume data of vascular enhanced phase. Practically, extensive 3D image data of a target organ generated by the image data generation unit 6 based on volume data sequentially supplied from the volume data generation unit 5 are successively displayed on the display unit 8. Under observation of the 3D image data, volume data of tumor enhanced phase and vascular enhanced phase selected among the time-series volume data are respectively stored in the volume data memory 71 in accordance with a selection command signal supplied from the input unit 9.

The vascular data detection unit 72 includes a vascular region detection unit 721 and a core line set up unit 722. The vascular region detection unit 721 detects vascular regions in the therapy target organ based on the volume data of the vascular enhanced phases. The core line set up unit 722 sets up each core line of the detected vascular regions. The vascular region detection unit 721 detects vascular regions by extracting volume data having larger voxel values than a designated threshold value due to the inflow of the contrast enhance agent. Thus, the vascular region detection unit 721 compares voxel values of the vascular enhanced phases read out from the volume data memory 71 with a threshold values $\alpha1$ supplied from the input unit 9 through the main control unit 10 and extracts voxel values larger than the threshold value $\alpha1$.

The core line set-up unit 722 arranges a reference point in the vascular region detected by the vascular region detection unit 721 and sets up a core line (a center line) of the vascular region by starting from the reference point. For instance, the core line set-up unit 722 generates a plurality of unit vectors in 3 dimensional directions from the reference point arranged in the vascular region and selects a searching vector among a plurality of unit vectors. Further, the core line set-up unit 722 calculates a position coordinate for a center of a vascular cross-sectional plane which orthogonally crosses the unit vector along a direction in which a distance to a boundary surface of the selected vascular region becomes the largest. Then, a corrected searching vector is newly set up at the center of vascular cross-sectional plane so that an intersectional crossing point between the searching vector and the vascular cross-sectional plane coincides with the center of gravity. Based on a plurality of gravity center position coordinates along the vascular running direction acquired by repeating this process, a core line of the vascular region is set up.

Figure 6:
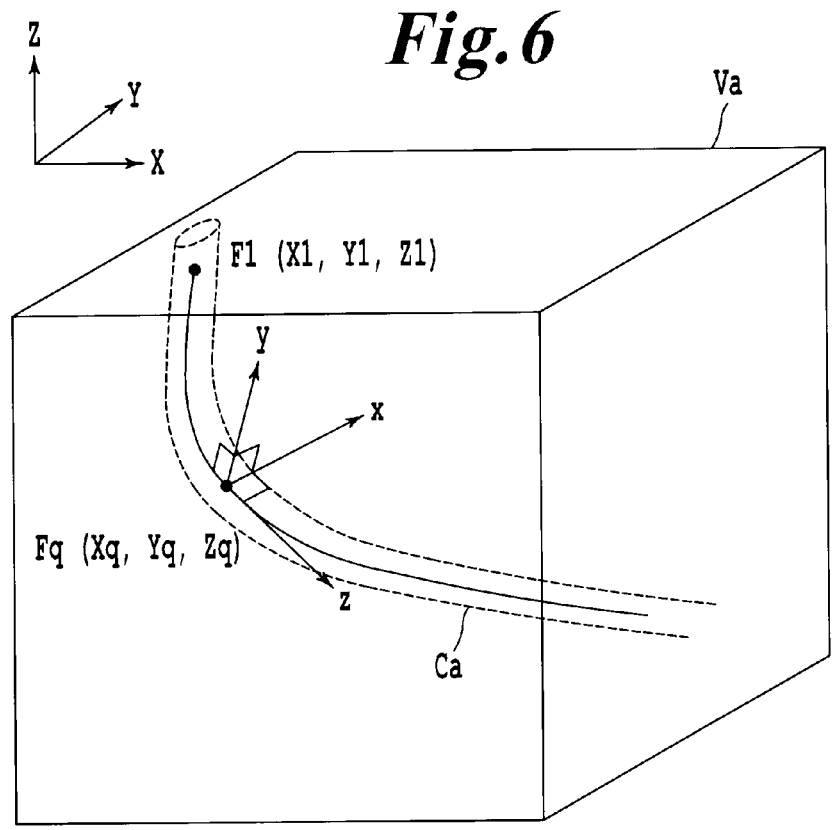
FIG. 6 illustrates a coordinate system for a core line set up by a core line set-up unit shown in FIG. 1.

FIG. 6 is an exemplary coordinate system for a core line Ca set up by the core line set-up unit 722 to the volume data Va of the vascular enhanced phase that is constructed by a plurality of voxels arranged in 3 dimensions. The core line Ca is set up by connecting a gravity center Fq (Xq, Yq, Zq) at a cross-section of the vascular lumen starting from a reference point F1 (X1, Y1, Z1) that is freely set up in the vascular region of the volume data Va.

Turning to FIG. 5, the tumor data detection unit 73 includes a tumor candidate region detection unit 731 and a tumor position data measurement unit 732. The tumor candidate region detection unit 731 detects a tumor candidate region in a therapy target organ based on the volume data of tumor enhanced phase. The tumor position data measurement unit 732 measures a gravity center position data of the detected tumor candidate region. The tumor candidate region detection unit 731 compares the voxel value having the volume data of the tumor enhanced phase supplied from the volume data memory 71 with threshold values $\alpha2$ and a $\alpha3$ ($\alpha2>\alpha3$) that are preliminarily set up in the input unit 9. Further, the tumor candidate region detection unit 731 detects a tumor candidate region by extracting a voxel that has a smaller value than the adjacent vascular regions and normal tissue regions when a contrast enhance agent is dosed. The tumor position data measurement unit 732 includes an arithmetic processing unit (not shown) for measuring a gravity center position data of a tumor candidate region based on the position coordinate of the voxel included in the tumor candidate region detected by the tumor candidate regions detection unit 731.

Figure 7:
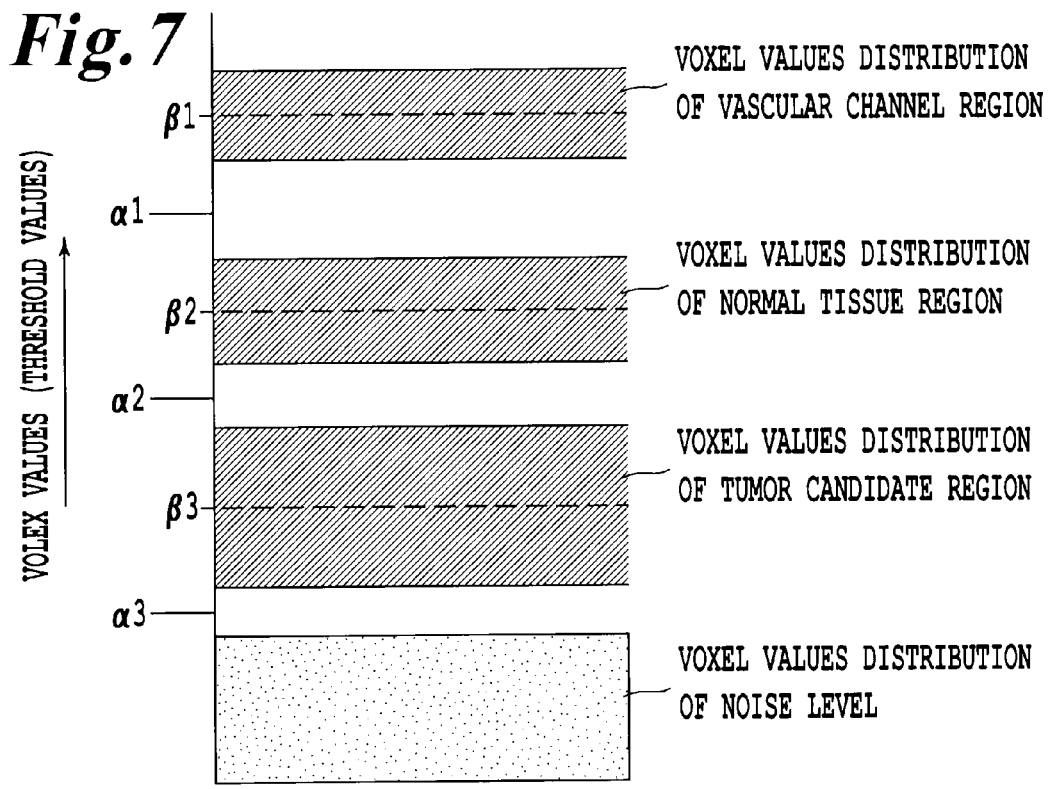
FIG. 7 is a graph depicting relationships between voxel value distributions of vascular regions and tumor candidate regions in the embodiment and threshold values set up for detecting these regions.

With reference to FIG. 7, these relationships explain in an exemplary case of MR imaging for a liver having inflow of Gd-EOB-DTPA as a therapy target organ. In this case, it is supposed that a value $\beta1$ is a mean voxel value of distributions for the vascular regions in the volume data of the vascular enhanced phases acquired through the MR imaging. $\beta2$ is a mean voxel value of the distributions of normal tissue region at the volume data of tumor enhanced phases and $\beta3$ is a mean voxel value of the distributions for the tumor candidate regions. The threshold values $\alpha1$ to $\alpha3$ are set up by the input unit 9 in order to detect the vascular regions and the tumor candidate regions. In case of MR imaging by using Gd-EOB-DTPA as a contrast enhance agent, the mean voxel value $\beta1$ of the vascular enhanced phase has the largest value. The mean voxel value $\beta2$ of the normal tissue region of the tumor enhanced phase follows the voxel value $\beta1$, and the mean voxel value $\beta3$ of the tumor candidate regions of the tumor enhanced phase are successively reduced. Accordingly, by setting threshold values $\alpha1$ to $\alpha3$ so as that $\beta1>\alpha1>\beta2>\alpha2>\beta2>\alpha3$ as illustrated in FIG. 7, the vascular region detection unit 721 in the vascular data detection unit 72 can detect vascular regions having larger voxel values than the threshold value α1. Further, the tumor candidate region detection unit 731 in the tumor data detection unit 73 can detect tumor candidate regions having smaller voxel values than the vascular regions or the normal tissue regions. In FIG. 7, the threshold values α3 is set up to exclude unnecessary voxels or noise level voxels which do not directly engage to the vascular regions or the tumor candidate regions.

Turning back to FIG. 5, the adjacent vascular detection unit 74 includes an arithmetic processing unit (not shown) for detecting each of vascular regions adjacent to each of the tumor candidate regions based on at least one of the tumor candidate region data detected by the tumor candidate region detection unit 731 and the vascular region data detected by the vascular regions detection unit 721. Thus, the arithmetic processing unit in the adjacent vascular detection unit 74 detects an adjacent core line located within a prescribed distance from a gravity center (each gravity center of the tumors) of the tumor candidate regions based on the core line data supplied from the core line set-up unit 722 in the vascular data detection unit 72. Further, the arithmetic processing unit detects each adjacent point on the adjacent core line located at the nearest position to each of the gravity center of the tumors based on each of the gravity center position data of the tumor candidate regions supplied from the tumor position data measurement unit 732 in the tumor data detection unit 73. Further, the arithmetic processing unit detects adjacent vascular regions corresponded to the detected adjacent core line.

Figure 8:
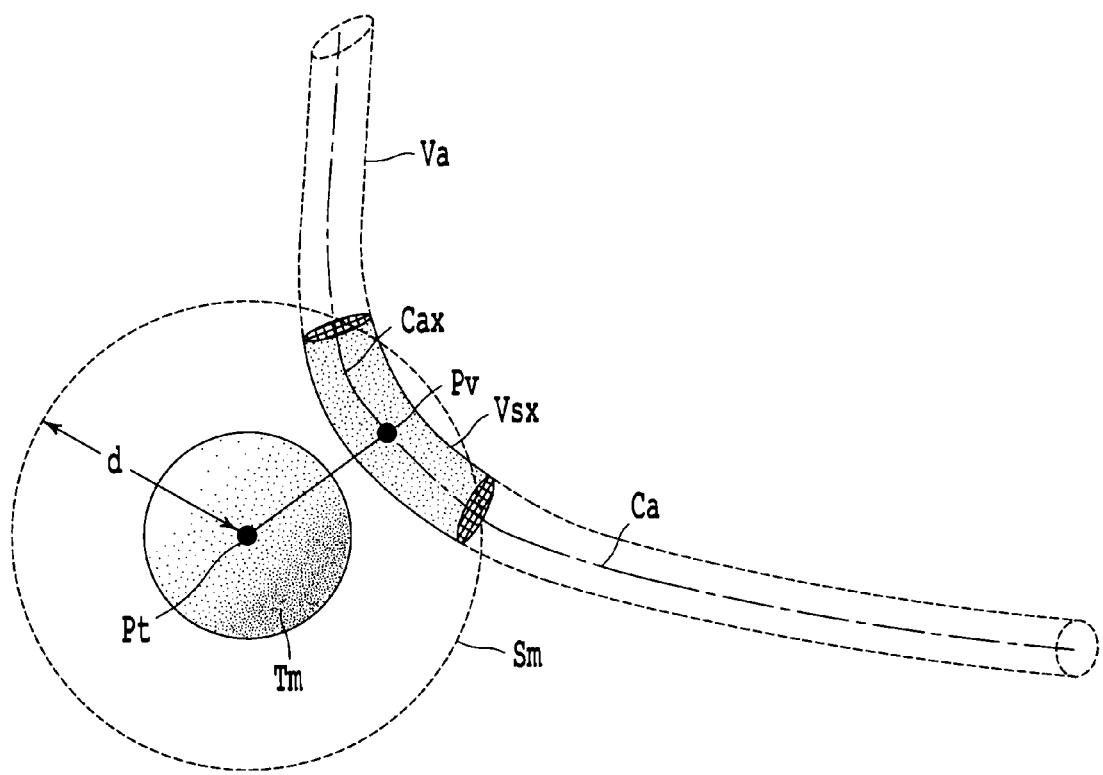
FIG. 8 is an exemplary model depicting an adjacent vascular detected by the adjacent vascular detection unit shown in FIG. 1.

FIG. 8 illustrates an exemplary model view of an adjacent vascular region detected by the adjacent vascular detection unit 74. The arithmetic processing unit in the adjacent vascular detection unit 74 sets up a spherical surface Sm that has, as a reference, a prescribed radius d from each gravity center of the tumor Pt of the tumor candidate region Tm. The arithmetic processing unit detects a core line Ca of a vascular region Vs located in the spherical surface Sm as an adjacent core line Cax. Next, the arithmetic processing unit detects an adjacent point Pv on the nearest adjacent core line to each gravity center of the tumor Pt. Further, the arithmetic processing unit detects an adjacent vascular region Vsx having an adjacent core line Cax as a gravity center axis.

Again turning to FIG. 5, the tumor parameter calculation unit 75 includes, for instance, a branch data detection unit 751, a stenosis rate measuring unit 752 and a tumor calculation unit 753 for calculating various tumor parameters based on adjacent vascular data supplied from the adjacent vascular detection unit 74, vascular regions data supplied from the vascular data detection unit 72 and tumor candidate regions data supplied from the tumor data detection unit 73 in order to set up recommended therapy methods.

Figure 9:
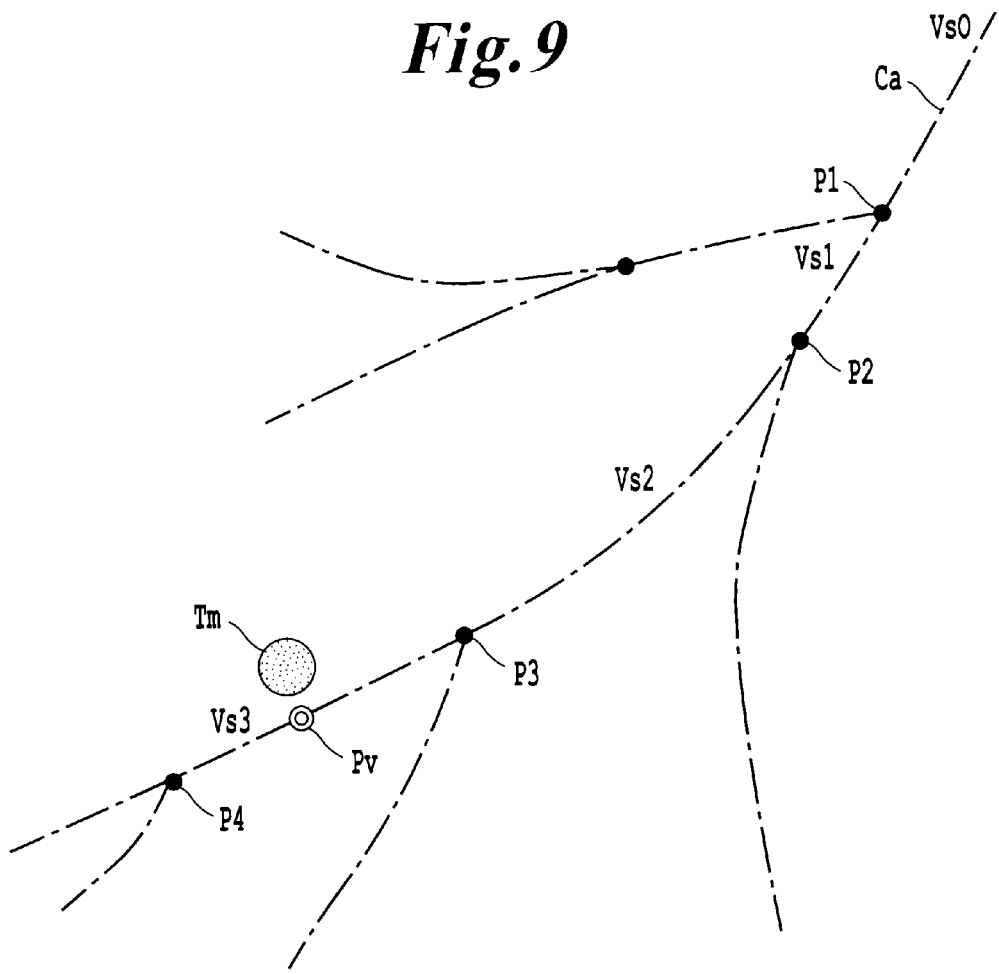
FIG. 9 depicts branch data at adjacent points detected by the branch data detection unit show in FIG. 1.

As illustrated in FIG. 9, the branch data detection unit 751 detects a branch to which the adjacent point Pv belongs based on an adjacent point Pv on an adjacent core line supplied from the adjacent vascular detection unit 74 and a core line Ca supplied from the core line set-up unit 722 in the vascular data detection unit 72. For instance, supposing that a main trunk Vs0 of a vascular region Vs extends until a first branch point P1 of the core line Ca, a first branch Vs1 extends from the first branch point P1 to a second branch point P2, a second branch Vs2 locates from the second branch point P2 to a third branch point P3, a third branch Vs3 exists from the third branch point P3 to a fourth branch point P4 and so on, the branch data detection unit 751 receives a position data of the adjacent point Pv supplied from the adjacent vascular detection unit 74 and a position data of core line Ca supplied from the core line set-up unit 722 in the vascular data detection unit 72, and detects a third branch Vs3 in which the adjacent point Pv is belonged by tracking back the core line Ca starting at the adjacent point Pvs.

The stenosis rate measuring unit 752 receives a position data of the adjacent core line supplied from the adjacent vascular detection unit 74 and an outline data of the vascular region supplied from the blood vessels region detection unit 721, and measures a stenosis rate at the adjacent vascular region by setting up an outline data of the vascular region to a plurality of cross-sectional planes perpendicular to the adjacent core line.

Figure 10:
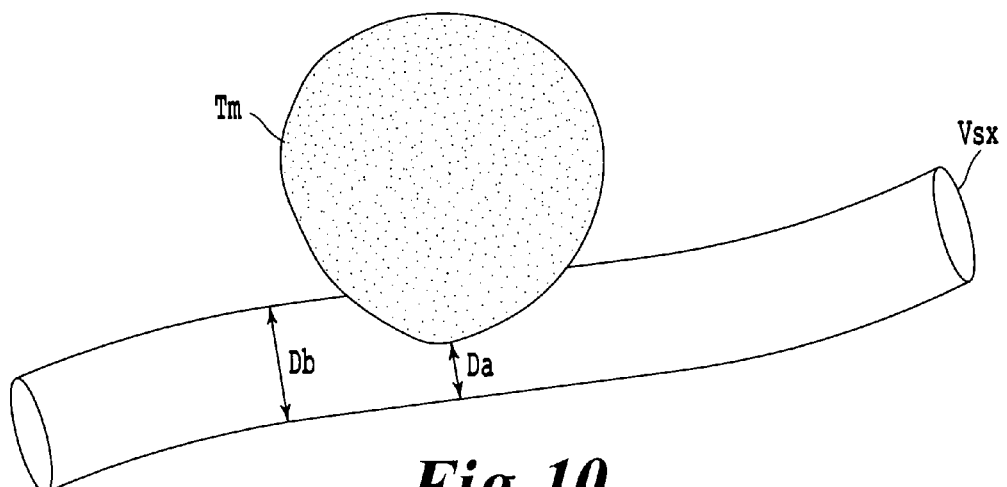
FIG. 10 depicts a stenosis rate of an adjacent vascular region measured by the stenosis rate measuring unit shown in FIG. 1.

Thus, as illustrated in FIG. 10, the stenosis rate measuring unit 752 measures an inner radius Da of a vascular portion where a stenosis occurs in the adjacent vascular Vsx due to invasion of the adjacent tumor candidate region Tm detected by the adjacent vascular detection unit 74 and an inner radius Db of a normal vascular portion. Further, the stenosis rate measuring unit 752 measures stenosis rates at the adjacent point Pv of the adjacent point Pv and the near points based on the measurements of radiuses.

Turning to FIG. 5, the tumor measurement unit 753 in the tumor parameter calculation unit 75 measures a tumor radius and a number of tumors based on outline data of tumor candidate regions supplied from the tumor candidate regions detection unit 731 in the tumor data detection unit 73. The therapy method set up unit 76 includes a therapy algorithm storage unit 761 and a therapy method selection unit 762 for setting up appropriate recommended therapy methods of policies for the tumor therapy based on various tumor parameters calculated in the tumor parameter calculation unit 75. The therapy algorithm storing unit 761 stores therapy algorithm preliminarily set up based on the therapy experiences.

Figure 11:
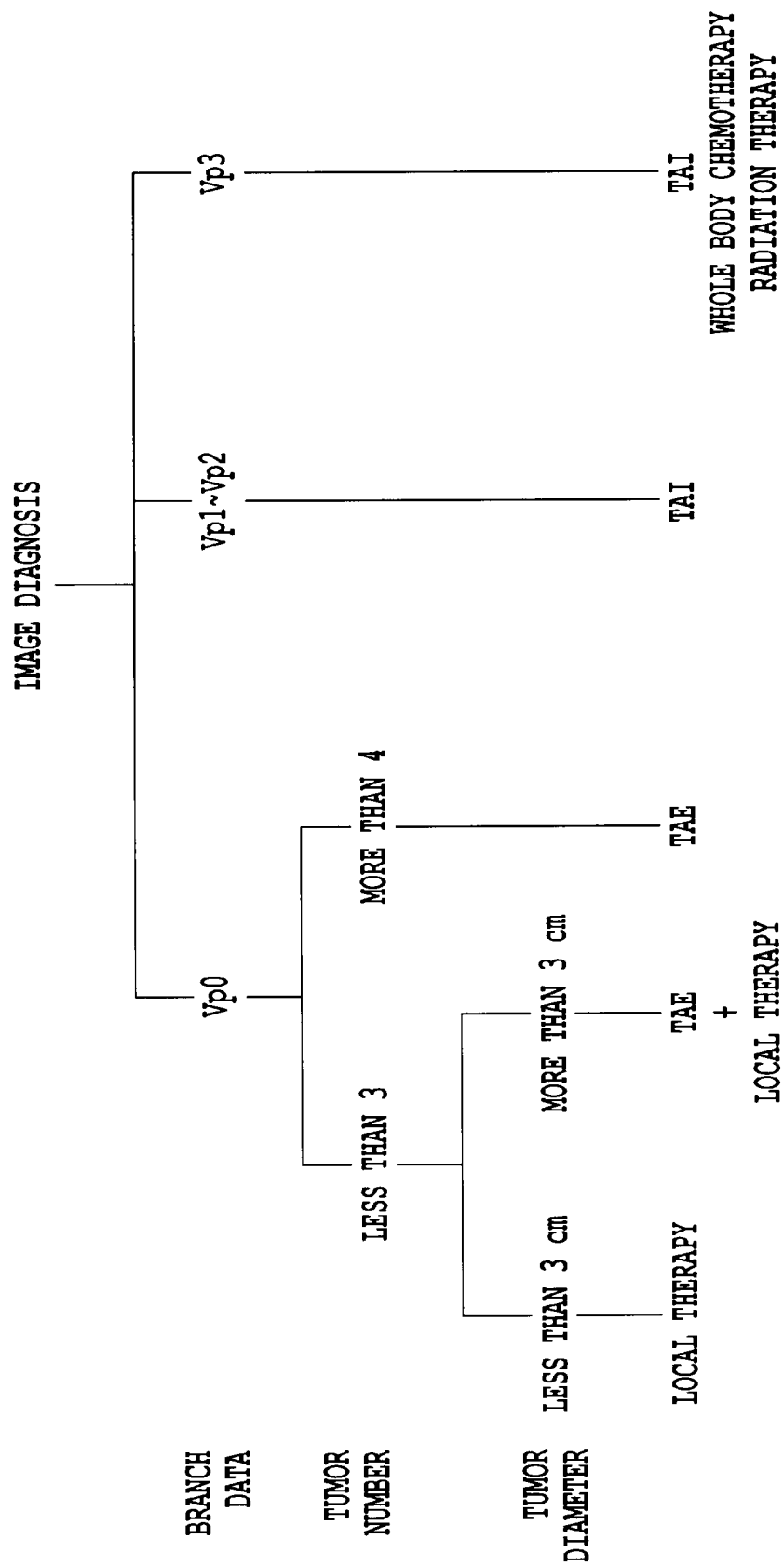
FIG. 11 is an exemplary therapy algorithm used for setting up recommended therapy methods in the embodiment shown in FIG. 1.

FIG. 11 depicts an exemplary efficacious therapy algorithm for setting up recommended therapy methods for a hepatocellular cancer. In here, recommended therapy methods are set up based on branch data of adjacent points, a number of tumors and a tumor radius. Thus, the therapy methods are classified into a Vp0 where an adjacent vascular region (a portal vein) and adjacent points do not exist at the near position to tumor candidate regions, a Vp1 where adjacent points exist at the periphery from the portal vein second branch, a Vp2 where adjacent points exist at the portal vein second branch, a Vp3 where adjacent points exist at the portal vein first branch and a Vp4 (not shown) where adjacent points exist at a main trunk of the portal vein. At the Vp1 and Vp2 where adjacent points exist at the portal vein branch, the trans-catheter liver artery infusion (TAI) therapy is selected, and at the Vp3, such as the TAI therapy and the whole body chemo-therapy are selected.

At the Vp0 where adjacent portal vein and adjacent points do not exist near to the tumor candidate region, the therapy methods are further classified based on the number of tumors and the tumor radius. When more than 4 tumors exist, the trans-catheter liver artery embolization (TAE) therapy is selected. When the tumor number is less than 3 and a tumor radius is larger than 3 cm, a local therapy, such as the TAE therapy or the radio frequency ablation (RFA) therapy is selected. When the tumor number is less than 3 and a tumor radius is less than 3 cm, a local therapy is selected.

The therapy method selection unit 762 in the therapy method set up unit 76 receives branch data of adjacent points, stenosis rate data at adjacent vascular, and numbers data and diameters data of tumor candidate regions that are supplied from the tumor parameter calculation unit 75. The therapy method selection unit 762 sets up recommended therapy methods corresponded to these data by selecting among various therapy methods preliminarily stored in the therapy algorithm storing unit 761. The acquired recommended therapy methods data are displayed on the display unit 8 as a second therapy assist data for the tumor therapy.

Turning to FIG. 1, the display unit 8 in the medical image diagnosis apparatus 200 includes a display data generation unit, a data conversion unit and a monitor (all not shown). The display data generation unit generates display data by adding supplementary data, such as patient data and outline data of tumor candidate regions, to the 3D image data supplied from the image data generation unit 6 and MPR image data. The data conversion unit performs conversion processes, such as digital/analog (D/A) conversion and television format conversion, to the display data generated by the display data generation unit for displaying on the monitor as the first therapy assist data for the tumor therapy. Similarly, the display data generation unit converts the data relating to the recommended therapy methods from supplied the therapy method set up unit 76 in the data process unit 7 to a prescribed display format for displaying the second therapy assist data for the tumor therapy on the monitor.

The input unit 9 includes input devices, such as a display panel, switches, key board and a mouse, on a operation console for performing input of patient data, setting up of volume data acquisition conditions and image data generation conditions, designating tumor enhanced phase and vascular enhanced phase, and setting up threshold values for detecting vascular regions and tumor candidate regions, and input of various command signals.

The main control unit 10 includes a central processing unit (CPU) and a memory circuit (both not shown) to totally control each unit provided in the medical image diagnosis apparatus 200. The memory circuit in the main control unit 10 stores input data and set up data from the input unit 9. The CPU in the main control unit 10 processes image data acquired through the image data acquisition unit 100 based on the input data and set up data stored in the memory unit and generates a wide 3D image data to the therapy target organ of the patient and a narrow scope 3D image data and MPR image data centering around the tumor candidate region of the target organ for displaying. Further, the CPU performs setting up and display of appropriate therapy methods for the tumor therapy based on the tumor candidate regions detected from the volume data at tumor enhanced phase and vascular advanced phase, and shape data and position data of adjacent vascular regions to the tumor candidate regions.

Figure 12:
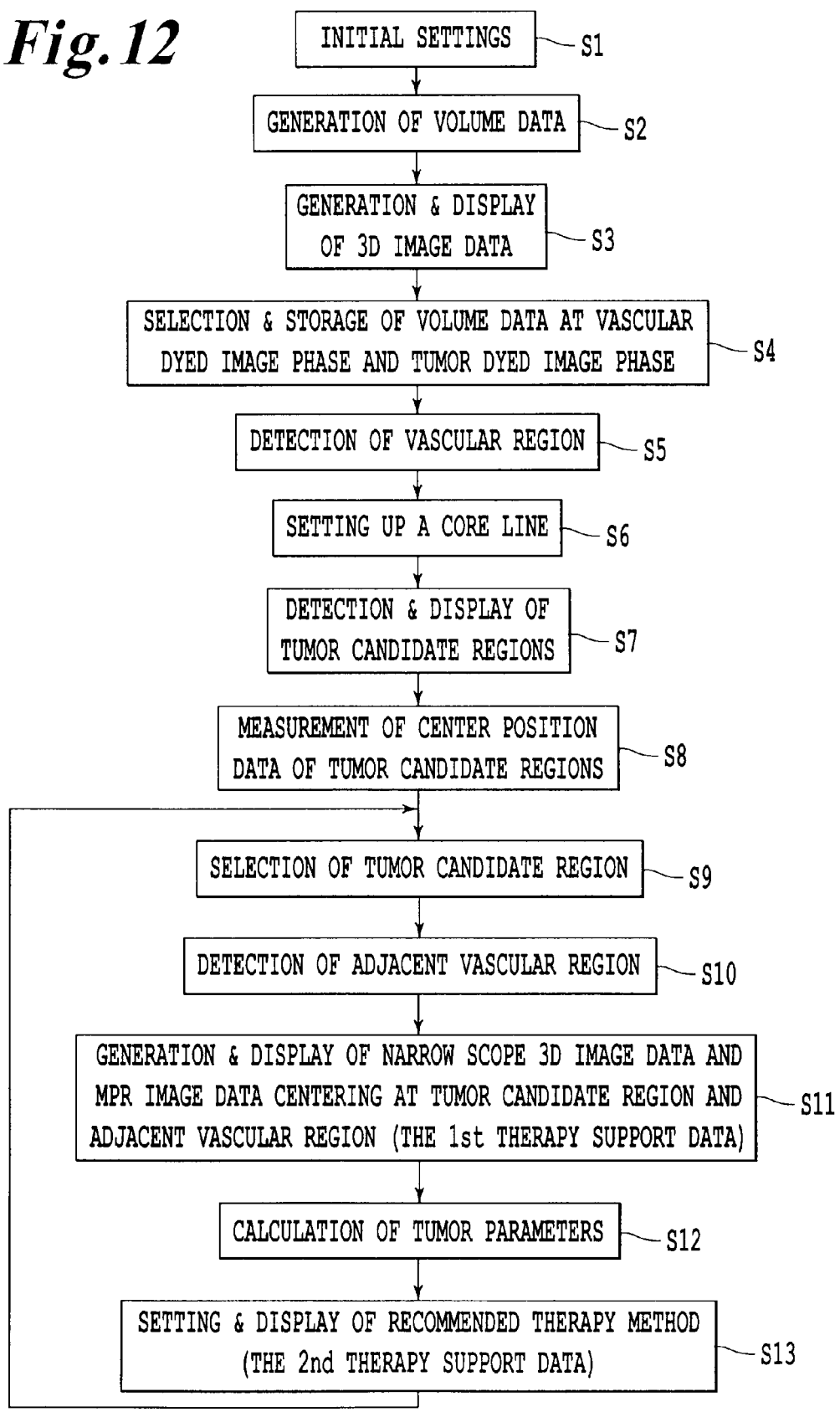
FIG. 12 is a flowchart illustrating a process for generating and displaying therapy assist data in the embodiment shown in FIG. 1.

FIG. 12 is a flowchart illustrating generation of image data and setting up and displaying processes of the therapy method based on the volume data acquired by MR imaging consistent with the present embodiment. Of course, the volume data can be acquired through other imaging, such as an X-ray CT imaging. Prior to acquisition of volume data the patient, an operator, such as a doctor or a laboratory technician, of the medical image diagnosis apparatus 200 executes an initial setting up operation at the input unit 9, such as an input of patient data, setting up of volume data acquisition conditions and image data generation conditions, and setting up of threshold values for detecting vascular regions and tumor candidate regions (FIG. 12, step S1).

When the initial setting up has finished, a contrast enhance agent is administered to a patient 150. When a prescribed time has passed after the administration of the contrast enhance agent, an MR imaging start command is input through the input unit 9. The image data acquisition unit 100 receives the start command signal through the main control unit 10 and performs MR imaging under a prescribed pulse sequence based on the volume data acquisition conditions to the patient 150 for acquiring MR data. The volume data generation unit 5 generates volume data of real space by performing reconstruction processing of a 2D Fourier transform or a 3D Fourier transform and interpolation process to the MR data of 3D frequency space (k space) supplied from the image data acquisition unit 100 (FIG. 12, step S2).

Then, the 3D image data generation unit 61 in the image data generation unit 6 sets up opacity and color tones for the voxels of the volume data supplied in time series from the volume data generation unit 5 and generates 3D image data by performing a rendering process. The generated 3D image data is displayed on a monitor in the display unit 8 (FIG. 12, step S3).

While observing 3D image data displayed on the display unit 8, the operator designates a tumor enhanced phase where a time phase of a tumor region is dyed by a contrast enhance agent and a vascular enhanced phase where a prescribed vascular region is dyed by the contrast enhance agent through the input unit 9. Thus, volume data of tumor enhanced phase and vascular enhanced phase are selected among the plurality of volume data supplied from the generation unit 5. Each selected volume data of each time phase is stored in the volume data memory 71 in the data process unit 7 (FIG. 12, step S4).

After finishing the selection and storing the volume data of the tumor enhanced phase and the vascular enhanced phase, the vascular region detection unit 721 in the vascular data detection unit 72 compares a voxel value for the volume data of vascular enhanced phase read out from the volume data memory 71 with the threshold value a1 supplied from the input unit 9 through the main control unit 10. A vascular region is detected by extracting a voxel having a larger value than the threshold value $\alpha 1$ due to the administration of the contrast enhance agent (FIG. 12, step S5). Then, the core line set-up unit 722 provides a reference point in the vascular region detected by the vascular region detection unit 721, and sets up a core line of the vascular region starting at the reference point (FIG. 12, step S6).

The tumor candidate region detection unit 731 in the tumor data detection unit 73 compares the voxel value for the volume data of tumor enhanced phase supplied from the volume data memory 71 and the threshold values $\alpha 2$ and $\alpha 3$ ($\alpha 2 > \alpha 3$) supplied from the input unit 9 through the main control unit 10, and detects at least one tumor candidate region by extracting a voxel having a smaller value than that of the adjacent vascular regions and normal tissue regions when the contrast enhance agent is administered. By receiving the result of the detection, the display data generation unit in the display unit 8 overlaps, for instance, a closed curve for indicating an outline of the tumor candidate region on the extensive 3D image data of the therapy target organ generated by the 3D image data generation unit 61 in the image data generation unit 6 based on the volume data of tumor enhanced phase read out from the volume data memory 71 for displaying on the monitor (FIG. 12, step S7).

The tumor position data measurement unit 732 measures each gravity center of the tumors position data of the tumor candidate region based on the position coordinate of voxel included in the tumor candidate region detected by the tumor candidate region detection unit 731 (FIG. 12, step S8). Then the operator selects a desired tumor candidate region among the tumor candidate regions displayed on the display unit 8 together with the extensive 3D image data of tumor enhanced phase by using an input device provided in the input unit 9 (FIG. 12, step S9).

By receiving a tumor candidate region selection signal through the main control unit 10, the adjacent vascular detection unit 74 in the data process unit 7 detects adjacent core lines existing within a prescribed scope of distance from the each gravity center of the tumors and an adjacent point positioned at the most adjacent core line to the each gravity center of the tumors based on the core line position data supplied from the core line set-up unit 722 in the vascular data detection unit 72 and a gravity center position data of the tumor candidate region supplied from the tumor position data measurement unit 732 in the tumor data detection unit 73 corresponding to the selection signal. Further, the adjacent vascular detection unit 74 detects vascular regions corresponding to the detected adjacent core line as the adjacent vascular regions (FIG. 12, step S10).

Then, the MPR image data generation unit 62 in the image data generation unit 6 receives a gravity center position data of the tumor candidate region supplied from the tumor data detection unit 73 in the data process unit 7 and a position data of the adjacent core line to the tumor candidate region supplied from the adjacent vascular detection unit 74. Further, the MPR image data generation unit 62 sets up a plane surface MPR cross-section or a curved surface MPR cross-section which includes the each gravity center of the tumors and the adjacent core line to the volume data of the tumor enhanced phase or the vascular enhanced phase that are read out from the volume data memory 71. By extracting a voxel of the volume data existing on the MPR cross-section, a narrow scope MPR image data is generated at each center of the tumor candidate region and the adjacent vascular region.

The 3D image data generation unit 61 in the image data generation unit 6 receives a gravity center position data of the tumor candidate region supplied from the tumor data detection unit 73 in the data process unit 7 or a position data of the adjacent point supplied from the adjacent vascular detection unit 74. By performing a rendering process for the volume data of the tumor enhanced phase or the vascular enhanced phase read out from the volume data memory 71 at the each gravity center of the tumors or an adjacent point, a narrow scope 3D image data is generated with centering the tumor candidate region and the adjacent vascular region. The acquired MPR image data and 3D image data are displayed on a monitor in the display unit 8 as the first therapy assist data for the tumor therapy (FIG. 12, step S11).

The branch data detection unit 751 branch data detection unit 751 in the tumor parameter calculation unit 75 detects a branch including the adjacent point based on a position data of the adjacent point supplied from the adjacent vascular detection unit 74 and a position data of the extensive core line including the adjacent point supplied from the core line set-up unit 722. The stenosis rate measuring unit 752 receives a position data of the adjacent core line supplied from the adjacent vascular detection unit 74 and an outline data of the vascular region supplied from the blood vessels region detection unit 721, and sets up a plurality of cross-sections orthogonal to the adjacent core line to the outline data of the vascular region. Then, a stenosis rate at the adjacent vascular region is calculated by measuring an inner radius of the vascular region in which a stenosis is generated due to tumor invasion and an inner radius of a normal vascular region. The tumor measurement unit 753 measures tumor number and a tumor radius based on the outline data of the tumor candidate region supplied from the tumor candidate region detection unit 731 in the tumor data detection unit 73 (FIG. 12, step S12).

The therapy method set up unit 76 receives tumor parameters, such as branch data of adjacent points calculated in the tumor parameter calculation unit 75, stenosis rate at adjacent vascular, and number and each tumor radius of tumor candidate regions. Then the therapy method set-up unit 76 sets up an appropriate therapy policy for the tumor by selecting one or more therapy methods corresponding to these tumor parameters among various therapy methods preliminary stored in the therapy algorithm storing unit 761. The set-up therapy method data is displayed on a monitor in the display unit 8 as a second therapy assist data for the tumor therapy together with the first therapy assist data generated in the step S11, i.e., the narrow scope 3D image data and MPR image data (FIG. 12, step S13).

When generation/display of a narrow scope 3D image data and MPR image data centering around the tumor candidate regions and the adjacent vascular regions and setting up/display of therapy method for the tumor candidate regions have completed, by returning display mode for overlapping outline data of the tumor candidate regions to the extensive 3D image data of the therapy target organ in step S7, new tumor candidate regions are successively selected among a plurality of displayed tumor candidate regions. To each of the selected tumor candidate regions, generation/display of narrow scope 3D image data and MPR image data, and setting up/display of therapy method for the tumor candidate regions are performed (FIG. 12, steps S9 to S13).

Figure 13:
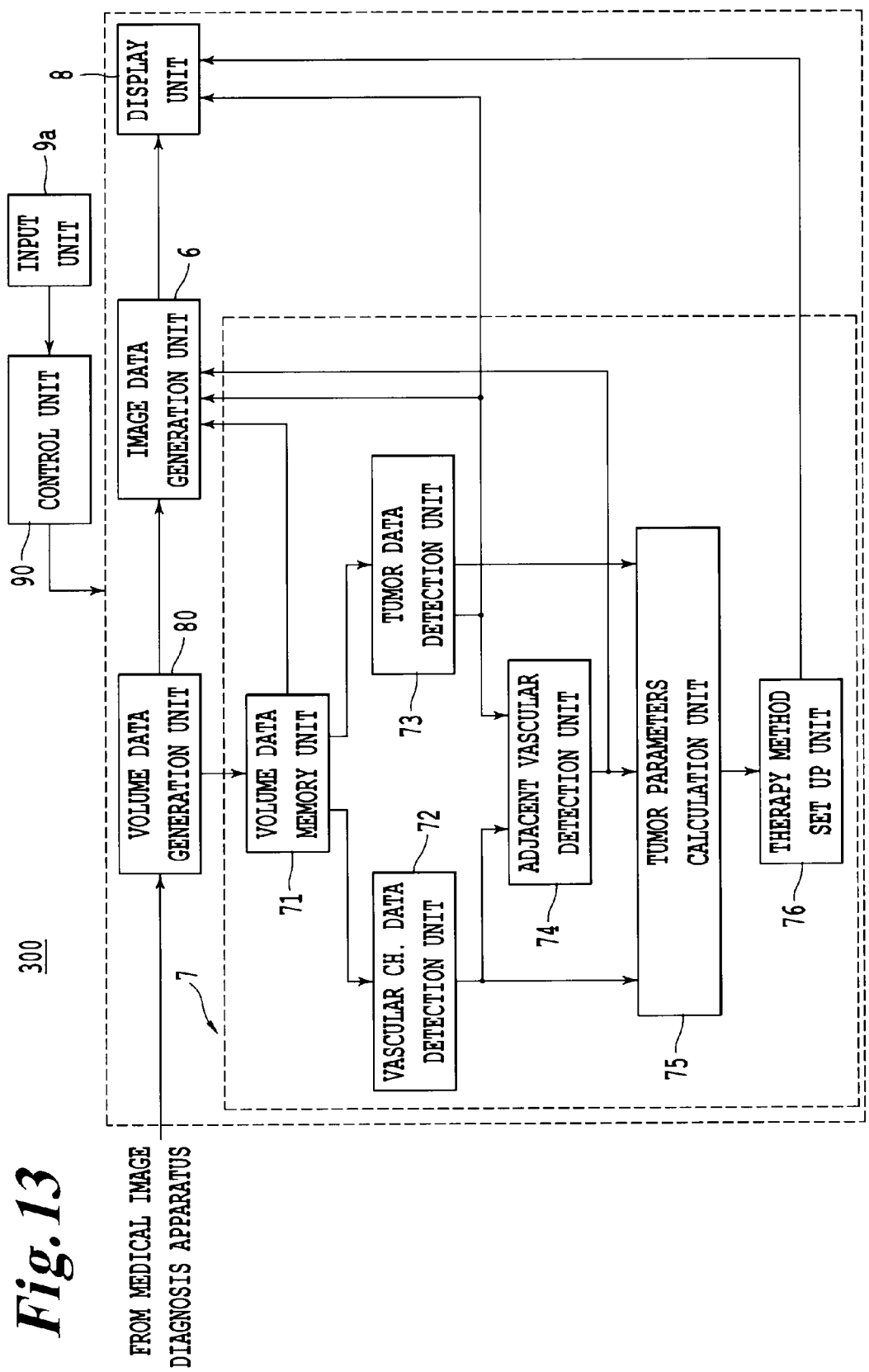
FIG. 13 is a block diagram illustrating an image data processing apparatus according to another embodiment of the present invention.

FIG. 13 is a block diagram illustrating a construction of another embodiment of an image data processing apparatus according to the present invention. In the image data processing apparatus consistent with this embodiment, 3D image data of a narrow scope and MPR image data for each of tumor candidate regions are generated and displayed by using volume data acquired through a medical image diagnosis apparatus provided at another place. Further, the image data processing apparatus sets up and displays appropriate recommended therapy methods for the tumor candidate regions. In FIG. 13, each unit having the same construction and the same function with the unit shown in FIG. 1 is applied the same number to avoid repetition of the same explanation.

The image data processing apparatus 300 consistent with the present embodiment includes a volume data storage unit 80, an image data generation unit 6, a data processing unit 7, a display 8, an input unit 9a and a control unit 90. The volume data storage unit 80 stores volume data of a dosed patient acquired in a time-series through a medical image diagnosis apparatus, such as an MRI apparatus and an X-ray CT apparatus (not shown) that may be provided at another location and supplied through a network or a large capacity storage. The image data generation unit 6 processes the volume data and generates an extensive 3D image data to the therapy target organ and a narrow scope 3D image data and MPR image data having a gravity center at the tumor candidate region of the therapy target organ. The data processing unit 7 detects tumor candidate regions and adjacent vascular regions to the tumor candidate regions in the therapy target organ by processing the volume data. Based on various data of the acquired tumor candidate regions and vascular regions, the data processing unit 7 sets up recommended therapy methods. The display unit 8 displays 3D image data and MPR image data generated in the image data generation unit 6 and the data of recommended therapy methods set up in the data process unit 7 as therapy assist data for the tumor therapy. The input unit 9a includes various input devices for performing input of a patient data, setting up of image data generation conditions, designating tumor enhanced phase and vascular enhanced phase, setting up of threshold values for detecting vascular regions and tumor candidate regions, and inputting various command signals. The control unit 90 includes a CPU and a memory circuit for totally controlling each unit in the image data processing apparatus 300.

The memory circuit in the control unit 90 stores the input data and the set up data trough the input unit 9*a*. The CPU in the control unit 90 processes volume data read out from the volume data storage unit 80 in time series based on the input data and set up data stored in the memory circuit for generating and displaying an extensive 3D image data for the therapy target organ and narrow scope 3D image data and MPR image data having a gravity center at a tumor candidate region of the therapy target organ. Further, the CPU detects the tumor candidate regions and the adjacent vascular regions based on the volume data of the tumor enhanced phases and the vascular enhanced phases for setting up and displaying the recommended therapy methods based on the size and position data of the detected tumor candidate regions and the adjacent vascular regions. The therapy assist data generation steps performed by the image data processing apparatus 300 substantially follow the same steps S3 to S13 explained in FIG. 12.

According to this embodiment of the present invention, efficacious therapy assist data of the therapy for the tumor occurred in the therapy target organ can be generated and displayed based on volume data acquired from a therapy target organ in a patient. Consequently, an appropriate therapy method for the tumor can be decided in a short time. Thus, efficient therapy can be achieved. Thus, by observing a narrow scope 3D image data having a gravity center at the tumor candidate region, each gravity center of the tumor candidate regions and a narrow scope MPR image data generated at an MPR cross-section plane including core lines of adjacent vascular regions to the tumor candidate regions, the tumor status of invasion into the vascular region can be accurately comprehended. Thus, an appropriate therapy method can be easily selected.

According to the embodiment of the present invention, various tumor parameters are calculated based on the shapes and position data of the tumor candidate regions and the adjacent vascular regions to the tumor candidate regions. Based on these tumor parameters and the preliminary set up therapy algorithm, an appropriate recommended therapy method for the tumor therapy is set up in a short time. Consequently, while a plurality of tumor candidate regions exists in the therapy target organ of the patient, the most appropriate recommended therapy method for each of the tumor candidate regions can effectively be set up.

By observing the first therapy assist data based on the above-mentioned narrow scope 3D image data and MPR image data and the second therapy assist data based on the recommended therapy methods, an operator for the tumor therapy can decide an appropriate therapy method for the tumor therapy in a short time.

In particular, since the adjacent vascular region is detected based on the core line of the vascular region locating within a prescribed range from the each gravity center of the tumors, the existence of tumors that have a possibility of invasion into the vascular can be easily discriminated. Further, it becomes possible to accurately recognize a progress level and a malignant level of the tumor to the vascular by calculating various tumor parameters based on the number data of the tumor candidate regions and the position data of the adjacent vascular regions to the tumor candidate regions.

According to the another embodiment of the present invention, the first and second therapy assist data can be generated and displayed by using volume data of the patient supplied through a medical image diagnosis apparatus provided at another place or a network. Consequently, the medical staff can decide the therapy policy or the therapy method for the patient without disturbing restrictions of time or places.

The present invention is not limited to the above-mentioned embodiments but it is also possible to apply some modifications. In the above-mentioned embodiments, the therapy assist data is generated and displayed based on the volume data acquired through MR imaging to the therapy target organ. Of course, it is possible to use volume data that is acquired through another imaging method, such as an X-ray CT imaging.

In the above-mentioned embodiments, a tumor enhanced phase and a vascular enhanced phase are designated through the input unit under observing 3D image data displayed on the display unit. Based on the designation signal, volume data of the tumor enhanced phase and the vascular enhanced phase are selected in time series among the plurality of volume data. It is also possible to newly provide a volume data selection unit for automatically selecting volume data of which voxel values of a prescribed vascular region and tumor candidate region have the maximum or the minimum volume data as the vascular enhanced phase and the tumor enhanced phase.

In the above embodiments, the first therapy assist data based on a narrow scope 3D image data and MPR image data having a gravity center at the tumor candidate region and the second therapy assist data including the recommended therapy method data are simultaneously displayed on the display unit 8. It is also possible to independently display the first therapy assist data and the second therapy assist data. Further it is possible to generate and display either one of the therapy assist data. Either one of 3D image data or MPR image data can be used as the first therapy assist data.

In the above embodiments, the branch data detection unit 751 detects a branch belonging the adjacent point on the adjacent core line as branch data. It is also possible to detect a branch belonging on the adjacent core line or the adjacent vascular region as the branch data.

In the embodiment, the tumor parameter calculation unit calculates branch data of adjacent points, a stenosis rate at an adjacent vascular, number of tumors and a tumor radius in tumor candidate regions based on adjacent vascular data supplied from the adjacent vascular detection unit, vascular regions data supplied from the vascular data detect and tumor candidate regions data supplied from the tumor data detect. Based on the results of these calculations, the therapy method set up unit sets up appropriate recommended therapy methods for the tumor therapy. Of course, it is also possible to set up the therapy method by using other therapy parameters.

While certain embodiments have been described, these embodiments are presented by way of example only, and are not intended to limit the scope of the invention. Indeed, the novel instruments described herein may be embodied in a variety of other forms; furthermore, various omissions and changes in the form of the instruments described herein may be made without departing from the spirit of the inventions. The accompanying claims and their equivalents are intended to cover such forms or modifications as would fall within the scope and spirit of the disclosed inventions.

The invention claimed is:

1. A medical image diagnosis apparatus comprising;
   a volume data generator including an image data memory configured to store image data sequentially acquired from a therapy target organ through an image acquisition device, a high speed arithmetic processor configured to generate 3D data based on the image data read out from the image data memory and an interpolation processor configured to generate volume data in time series based on the 3D data;
   a vascular region detector implemented by circuitry configured to detect vascular regions in the therapy target organ using volume data of vascular enhanced phases selected by processing circuitry from among the volume data generated in time series, the vascular enhanced phases corresponding to timings of brightness changes;

a tumor candidate region detector implemented by circuitry configured to detect tumor candidate regions in the therapy target organ using volume data of tumor enhanced phases selected by the processing circuitry from among the volume data generated in time series, the tumor enhanced phases corresponding to timings of brightness changes;

tumor position data measuring circuitry configured to detect each gravity center of the tumor candidate regions;

an adjacent vascular detector implemented by circuitry configured to
  obtain first information of the vascular regions detected by the vascular region detector and second information of the tumor candidate regions detected by the tumor candidate region detector, and
  detect, using the first and second information, the vascular regions adjacent to the tumor candidate regions that exist within a prescribed range from each gravity center of the tumors as adjacent vascular regions; and an image data generator implemented by circuitry configured to generate therapy assisting image data based on narrow scope volume data including the tumor candidate regions and the adjacent vascular regions extracted from the volume data.

2. The medical image diagnosis apparatus according to claim 1, wherein the image data generator generates at least either one of 3D image data or multi planar reconstruction (MPR) image data as the therapy assist data.

3. The medical image diagnosis apparatus according to claim 1, further comprising core line set-up circuitry configured to set up a core line to each of the vascular regions; and
  wherein the image data generator generates MPR image data on an MPR plane including the core line and each of the gravity center of the tumors.

4. The medical image diagnosis apparatus according to claim 1, further comprising a display configured to display the therapy assist data.

5. A medical image diagnosis apparatus comprising;
a volume data generator implemented by circuitry configured to generate volume data in time series from image data acquired with respect to a therapy target organ;
a vascular region detector implemented by circuitry configured to detect vascular regions in the therapy target organ using volume data of vascular enhanced phases selected by processing circuitry from among the volume data generated in time series, the vascular enhanced phases corresponding to timings of brightness changes;
a tumor candidate region detector implemented by circuitry configured to detect tumor candidate regions in the therapy target organ using volume data of tumor enhanced phases selected by the processing circuitry from among the volume data generated in time series, the tumor enhanced phases corresponding to timings of brightness changes;
tumor position data measuring circuitry configured to detect each gravity center of the tumor candidate regions;
an adjacent vascular detector implemented by circuitry configured to
  obtain first information of the vascular regions detected by the vascular region detector and second information of the tumor candidate regions detected by the tumor candidate region detector, and
  detect, using the first and second information, the vascular regions adjacent to the tumor candidate regions that exist within a prescribed range from each of the gravity center of the tumors;
a tumor parameter calculation calculator implemented by circuitry configured to calculate a tumor parameter based on at least either one of the tumor candidate region data, the vascular region data and the adjacent vascular region data; and
therapy method set-up processing circuitry configured to set up each therapy method for the tumor candidate regions based on the tumor parameter.

6. The medical image diagnosis apparatus according to claim 5, wherein the tumor parameter calculator calculates branch data of the vascular regions including the adjacent vascular regions or each stenosis rate of the adjacent vascular regions as the tumor parameter.

7. The medical image diagnosis apparatus according to claim 5, wherein the tumor parameter calculator calculates at least one of each tumor size of the tumor candidate regions and a number of tumor candidate regions as the tumor parameter.

8. The medical image diagnosis apparatus according to claim 5, wherein the therapy method set-up processing circuitry sets up the therapy method based on at least one of the calculated tumor parameters by the tumor parameter calculator and a preliminarily set up therapy algorithm.

9. The medical image diagnosis apparatus according to claim 5, further comprising a display configured to display the therapy method data as therapy assist data.

10. An image data processing apparatus comprising;
a volume data storage configured to store volume data acquired with respect to a therapy target organ in time series;
a vascular region detector implemented by circuitry configured to detect vascular regions in the therapy target organ using volume data of vascular enhanced phases selected by processing circuitry from among the volume data generated in time series, the vascular enhanced phases corresponding to timings of brightness changes;
a tumor candidate region detector implemented by circuitry configured to detect tumor candidate regions in the therapy target organ using volume data of tumor enhanced phases selected by the processing circuitry from among the volume data generated in time series, the tumor enhanced phases corresponding to timings of brightness changes;
tumor position data measuring circuitry configured to detect each gravity center of the tumor candidate regions;
an adjacent vascular detector implemented by circuitry configured to
  obtain first information of the vascular regions detected by the vascular region detector and second information of the tumor candidate regions detected by the tumor candidate region detector, and
  detect, using the first and second information, a vascular region adjacent to a tumor candidate region that is located within a prescribed range from the tumor gravity center; and
an image data generator implemented by circuitry configured to generate therapy assist data based on narrow scope volume data including the tumor candidate regions and the adjacent vascular region that are extracted from the volume data.

11. The image data processing apparatus according to claim 10, wherein the image data generator generates at least either one of 3D image data or multi planar reconstruction (MPR) image data as the therapy assist data.

12. The image data processing apparatus according to claim 10, further comprising a tumor parameter calculator implemented by circuitry configured to calculate a tumor parameter based on at least either one of the tumor candidate region data, the vascular region data and the adjacent vascular region data; and therapy method set-up processing circuitry configured to set up each therapy method for the tumor candidate regions based on the tumor parameter.

13. The image data processing apparatus according to claim 10, further comprising a display configured to display the therapy assist data.

* * * * *